United States Patent
MacDonald et al.

(10) Patent No.: US 7,141,518 B2
(45) Date of Patent: *Nov. 28, 2006

(54) DURABLE CHARGED PARTICLE COATINGS AND MATERIALS

(75) Inventors: John Gavin MacDonald, Decatur, GA (US); Kevin Peter McGrath, Alpharetta, GA (US); Bin Wu, Marietta, GA (US); Jaeho Kim, Roswell, GA (US); Lei Huang, Duluth, GA (US); Sharon Linda Greene, Canton, GA (US); Jeffrey Eldon Fish, Dacula, GA (US); Sheng-Hsin Hu, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/686,687

(22) Filed: Oct. 16, 2003

(65) Prior Publication Data

US 2005/0085144 A1  Apr. 21, 2005

(51) Int. Cl.
*B32B 9/00* (2006.01)
(52) U.S. Cl. .................. 442/59; 428/402; 428/403; 428/404; 428/357; 442/121
(58) Field of Classification Search ............... 428/357, 428/402, 403, 404; 442/59, 121
See application file for complete search history.

(56) References Cited

U.S. PATENT DOCUMENTS

| 2,015,864 | A | 10/1935 | Mëller et al. |
| 2,593,146 | A | 4/1952 | Howard |
| 3,266,973 | A | 8/1966 | Crowley |
| 3,338,992 | A | 8/1967 | Kinney |
| 3,341,394 | A | 9/1967 | Kinney |
| 3,381,688 | A | 5/1968 | Satas |
| 3,494,821 | A | 2/1970 | Evans |
| 3,502,538 | A | 3/1970 | Petersen |
| 3,502,763 | A | 3/1970 | Hartmann |
| 3,507,269 | A | 4/1970 | Berry |
| 3,542,615 | A | 11/1970 | Dobo et al. |
| 3,615,478 | A | 10/1971 | Hoshino et al. |
| 3,692,618 | A | 9/1972 | Dorschner et al. |
| 3,794,497 | A | 2/1974 | Pratt et al. |
| 3,802,817 | A | 4/1974 | Matsuki et al. |

(Continued)

FOREIGN PATENT DOCUMENTS

EP   0103214   3/1984

(Continued)

OTHER PUBLICATIONS

Abstract of Japanese Patent No. JP04255767, Sep. 10, 1992.

(Continued)

*Primary Examiner*—Cheryl A. Juska
*Assistant Examiner*—Arden B. Sperty
(74) *Attorney, Agent, or Firm*—Dority & Manning, PA

(57) ABSTRACT

This invention concerns coatings having high surface area materials and at least one metal ion adsorbed onto the high surface area material as well as substrates having the coating and methods of applying the coating. The substrates may be films, woven fabrics or may be nonwoven fabrics. The coatings have good odor and/or gas absorbing capabilities. Nonwoven fabrics include tissues, towels, coform materials, bonded carded webs, spunbond fabrics and so forth. The substrates may be made into storage and packaging material to reduce odor and retard the ripening of fruit. The substrates may be used in personal care products, to produce clothing for military and civilian applications and many other applications.

35 Claims, 5 Drawing Sheets

U.S. PATENT DOCUMENTS

| | | |
|---|---|---|
| 3,836,633 A | 9/1974 | Beschke |
| 3,849,241 A | 11/1974 | Butin et al. |
| 3,919,437 A | 11/1975 | Brown et al. |
| 3,960,494 A | 6/1976 | Verma et al. |
| 3,971,665 A | 7/1976 | Suzuki et al. |
| 4,006,030 A | 2/1977 | Yoshida et al. |
| 4,041,203 A | 8/1977 | Brock et al. |
| 4,078,029 A | 3/1978 | Yoshida et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| 4,297,233 A | 10/1981 | Gualandi |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A | 10/1983 | Tratnyek |
| 4,467,012 A | 8/1984 | Pedersen et al. |
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A * | 6/1985 | Hagiwara et al. ............ 428/198 |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara et al. |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |
| 4,818,464 A | 4/1989 | Lau |
| 4,823,404 A | 4/1989 | Morell et al. |
| 4,823,803 A | 4/1989 | Nakamura |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,064,599 A * | 11/1991 | Ando et al. .................. 264/237 |
| 5,100,581 A | 3/1992 | Watanabe et al. |
| 5,100,702 A | 3/1992 | Maeda et al. |
| 5,102,592 A * | 4/1992 | McCauley et al. ......... 501/97.2 |
| 5,108,739 A | 4/1992 | Kurihara et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,111 A | 4/1993 | Handjani et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,273,942 A * | 12/1993 | McCauley et al. ......... 501/97.1 |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Muller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai, et al. |
| 5,429,628 A | 7/1995 | Trinh et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A * | 1/1996 | Maruo et al. ............ 424/76.21 |
| 5,486,356 A | 1/1996 | Yim |
| 5,487,938 A | 1/1996 | Spencer et al. |
| 5,488,126 A | 1/1996 | Subramanian et al. |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,747,003 A | 5/1998 | Mohnot et al. |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |

| | | | | | | |
|---|---|---|---|---|---|---|
| 5,972,389 | A | 10/1999 | Shell et al. | 2002/0091071 A1 | 7/2002 | Fischer et al. |
| 5,985,229 | A | 11/1999 | Yamada et al. | 2002/0106466 A1 | 8/2002 | Hausmann et al. |
| 5,989,510 | A | 11/1999 | Abe et al. | 2002/0110686 A1 | 8/2002 | Dugan |
| 5,989,515 | A | 11/1999 | Watanabe et al. | 2002/0128336 A1 | 9/2002 | Kolb et al. |
| 6,004,625 | A | 12/1999 | Ohshima | 2002/0142937 A1 | 10/2002 | Carter et al. |
| 6,007,592 | A | 12/1999 | Kasai et al. | 2002/0149656 A1* | 10/2002 | Nohr et al. ............. 347/95 |
| 6,024,786 | A | 2/2000 | Gore | 2002/0150678 A1 | 10/2002 | Cramer et al. |
| 6,045,900 | A | 4/2000 | Haffner et al. | 2002/0176982 A1 | 11/2002 | Rohrbaugh et al. |
| 6,047,413 | A | 4/2000 | Welchel et al. | 2002/0177621 A1 | 11/2002 | Hanada |
| 6,060,410 | A | 5/2000 | Gillberg-LaForce et al. | 2002/0182102 A1 | 12/2002 | Fontenot et al. |
| 6,073,771 | A | 6/2000 | Pressley et al. | 2003/0013369 A1 | 1/2003 | Soane et al. |
| 6,075,179 | A | 6/2000 | McCormack et al. | 2003/0021983 A1 | 1/2003 | Nohr et al. |
| 6,096,299 | A | 8/2000 | Guarracino et al. | 2003/0050211 A1 | 3/2003 | Hage et al. |
| 6,111,163 | A | 8/2000 | McCormack et al. | 2003/0056648 A1 | 3/2003 | Fornai et al. |
| 6,172,173 | B1 | 1/2001 | Spencer et al. | 2003/0070782 A1 | 4/2003 | Proverb et al. |
| 6,177,608 | B1 | 1/2001 | Weinstrauch | 2003/0082237 A1 | 5/2003 | Cha et al. |
| 6,190,814 | B1 | 2/2001 | Law et al. | 2003/0100842 A1 | 5/2003 | Rosenberg et al. |
| 6,193,844 | B1 | 2/2001 | McLaughlin et al. | 2003/0147956 A1 | 8/2003 | Shefer et al. |
| 6,225,524 | B1 | 5/2001 | Guarracino et al. | 2003/0147966 A1 | 8/2003 | Franzen et al. |
| 6,238,767 | B1 | 5/2001 | McCormack et al. | 2003/0181540 A1 | 9/2003 | Quellet et al. |
| 6,254,894 | B1 | 7/2001 | Denkewicz, Jr. et al. | 2003/0203009 A1 | 10/2003 | MacDonald |
| 6,264,615 | B1 | 7/2001 | Diamond et al. | 2003/0235605 A1 | 12/2003 | Lelah et al. |
| 6,277,346 | B1 | 8/2001 | Murasawa et al. | 2004/0033269 A1 | 2/2004 | Hei et al. |
| 6,277,772 | B1 | 8/2001 | Gancet et al. | 2004/0034157 A1 | 2/2004 | Ghosh et al. |
| 6,291,535 | B1 | 9/2001 | Watanabe et al. | 2004/0043688 A1 | 3/2004 | Soerens et al. |
| 6,294,222 | B1 | 9/2001 | Cohen et al. | 2004/0122387 A1 | 6/2004 | Long et al. |
| 6,299,867 | B1 | 10/2001 | Aoyagi et al. | 2004/0175556 A1 | 9/2004 | Clark et al. |
| 6,309,736 | B1 | 10/2001 | McCormack et al. | 2004/0228963 A1* | 11/2004 | Bergh et al. ............. 427/64 |
| 6,315,864 | B1 | 11/2001 | Anderson et al. | 2005/0008861 A1* | 1/2005 | Yadav et al. ............. 428/403 |
| 6,334,988 | B1 | 1/2002 | Gallis et al. | 2005/0084632 A1* | 4/2005 | Urlaub et al. ............. 428/34.1 |
| 6,344,218 | B1 | 2/2002 | Dodd et al. | 2005/0112085 A1* | 5/2005 | MacDonald et al. ....... 424/76.1 |
| 6,344,272 | B1 | 2/2002 | Oldenburg et al. | 2005/0181067 A1* | 8/2005 | Yokoyama et al. ........ 424/641 |
| 6,358,537 | B1 | 3/2002 | Hoshino et al. | | | |
| 6,358,909 | B1 | 3/2002 | Ochomogo et al. | FOREIGN PATENT DOCUMENTS | | |
| 6,369,290 | B1 | 4/2002 | Glaug et al. | EP | 0232141 | 8/1987 |
| 6,376,741 | B1 | 4/2002 | Guarracino et al. | EP | 0251783 | 1/1988 |
| 6,387,495 | B1 | 5/2002 | Reeves et al. | EP | 0339461 | 11/1989 |
| 6,398,827 | B1 | 6/2002 | Ota et al. | EP | 0348978 A2 | 1/1990 |
| 6,410,765 | B1 | 6/2002 | Wellinghoff et al. | EP | 0376448 | 7/1990 |
| 6,425,530 | B1 | 7/2002 | Coakley | EP | 0389015 | 9/1990 |
| 6,427,693 | B1 | 8/2002 | Blackstock et al. | EP | 0389023 | 9/1990 |
| 6,428,814 | B1 | 8/2002 | Bosch et al. | EP | 0483500 A1 | 5/1992 |
| 6,433,243 | B1 | 8/2002 | Woltman et al. | EP | 0510619 A1 | 10/1992 |
| 6,440,187 | B1 | 8/2002 | Kasai et al. | EP | 0282287 | 4/1996 |
| 6,460,989 | B1 | 10/2002 | Yano et al. | EP | 0972563 | 1/2000 |
| 6,461,735 | B1 | 10/2002 | Furuya et al. | EP | 0749295 | 7/2000 |
| 6,467,897 | B1 | 10/2002 | Wu et al. | EP | 1034800 A1 | 9/2000 |
| 6,468,500 | B1 | 10/2002 | Sakaguchi et al. | EP | 1053788 | 11/2000 |
| 6,475,601 | B1 | 11/2002 | Sakaki et al. | EP | 1157672 | 11/2001 |
| 6,479,150 | B1 | 11/2002 | Liu et al. | EP | 1157672 A1 | 11/2001 |
| 6,491,790 | B1 | 12/2002 | Proverb et al. | EP | 1162172 A1 | 12/2001 |
| 6,498,000 | B1 | 12/2002 | Murasawa et al. | EP | 1188854 A1 | 3/2002 |
| 6,517,199 | B1 | 2/2003 | Tomioka et al. | EP | 1214878 A1 | 6/2002 |
| 6,531,704 | B1 | 3/2003 | Yadav et al. | EP | 1216675 A1 | 6/2002 |
| 6,536,890 | B1 | 3/2003 | Kato et al. | EP | 1298071 | 4/2003 |
| 6,548,264 | B1 | 4/2003 | Tan et al. | EP | 1315526 B1 | 6/2003 |
| 6,551,457 | B1 | 4/2003 | Westman et al. | JP | 62149322 | 7/1987 |
| 6,562,441 | B1 | 5/2003 | Maeda et al. | JP | 3221142 | 9/1991 |
| 6,575,383 | B1 | 6/2003 | Dobler et al. | WO | WO 8902698 A1 | 4/1989 |
| 6,578,521 | B1 | 6/2003 | Raymond et al. | WO | WO 9111977 A1 | 8/1991 |
| 6,589,562 | B1 | 7/2003 | Shefer et al. | WO | WO 9112029 A1 | 8/1991 |
| 6,607,711 | B1 | 8/2003 | Pedersen | WO | WO 9112030 A1 | 8/1991 |
| 6,623,848 | B1 | 9/2003 | Brehm et al. | WO | WO 9619346 A2 | 6/1996 |
| 6,638,918 | B1 | 10/2003 | Davison et al. | WO | WO 9619346 A3 | 6/1996 |
| 6,639,004 | B1 | 10/2003 | Falat et al. | WO | WO 9725076 A1 | 7/1997 |
| 6,645,569 | B1 | 11/2003 | Cramer et al. | WO | WO 98/20915 | 5/1998 |
| 6,693,071 | B1 | 2/2004 | Ghosh et al. | WO | WO 9820915 A1 | 5/1998 |
| 2001/0000889 A1 | | 5/2001 | Yadav et al. | WO | WO 98/26808 | 6/1998 |
| 2001/0023338 A1 | | 9/2001 | Guarracino et al. | WO | WO 9826808 A2 | 6/1998 |
| 2001/0031248 A1 | | 10/2001 | Hall-Puzio et al. | WO | WO 9826808 A3 | 6/1998 |
| 2001/0056246 A1 | | 12/2001 | Rodriguez-Fernandez | WO | WO 99/47252 | 9/1999 |
| 2002/0005145 A1 | | 1/2002 | Sherman | WO | WO 00/03797 | 1/2000 |
| 2002/0066542 A1 | | 6/2002 | Jakob et al. | | | |

| | | |
|---|---|---|
| WO | WO 0029036 A2 | 3/2000 |
| WO | WO 0029036 A3 | 3/2000 |
| WO | WO 00137764 A1 | 3/2000 |
| WO | WO 0059555 A1 | 10/2000 |
| WO | WO 00/76558 | 12/2000 |
| WO | WO 0076558 A1 | 12/2000 |
| WO | WO 01/06054 | 1/2001 |
| WO | WO 02/26272 | 4/2002 |
| WO | WO 02/49559 | 6/2002 |
| WO | WO 02/55115 | 7/2002 |
| WO | WO 02/62881 | 8/2002 |
| WO | WO 02/64877 | 8/2002 |
| WO | WO 02/83297 | 10/2002 |
| WO | WO 02/84017 | 10/2002 |
| WO | WO 02/95112 | 11/2002 |
| WO | WO 02094329 A1 | 11/2002 |
| WO | WO 03/00979 | 1/2003 |
| WO | WO 03/25067 | 3/2003 |
| WO | WO 03032959 A1 | 4/2003 |
| WO | WO 03088931 A2 | 10/2003 |
| WO | WO 03/92885 | 11/2003 |
| WO | WO 2004000986 A1 | 12/2003 |

OTHER PUBLICATIONS

Abstract of Japanese Patent No. JP05098185, Apr. 20, 1993.
Quincy, III, et al., U.S. Appl. No. 10/723,761, filed Nov. 26, 2004, Odor Control In Personal Care Products.
MacDonald, et al., U.S. Appl. No. 10/955,316, filed Sep. 30, 2004, Odor-Reducing Quinone Compounds.
Derwent Abstract, JP 5106199A, Apr. 1993, Nakajima et al.
Derwent Abstract, JP 9143872A, Jun. 1997, Sogawa.
Brunauer, S. et al., "Adsorption of Gases in Multimolecular Layers", *Journal of American Chemical Society*, vol. 60, Feb. 1938, pp. 309-319.
Béné, A. et al., "Applicability of a SPME Method for the Rapid Determination of VOCs", *Chimia*, 56, No. 6, 2002, ISSN 0009-4293, pp. 289-291.
Malik, D.J. et al., "Characterisation of Novel Modified Active Carbons and Marine Algal Biomass for the Selective Adsorption of Lead", *Water Research*, 36, 2002, pp. 1527-1538.
Cost, F., *Pocket Guide to Digital Printing*, Delmar Publishers, Albany, NY, ISBN 0-8273-7592-1, pp. 144-145.
Noller, C.R., "Saponins and Sapogenins. VIII. Surface Films of Echinocystic Acid and Derivatives", *The Journal of the American Chemical Society*, vol. 60, 1938, 3 pages.
Antonietti, M., "Synthesis of porous Silica with help from cyclodextrin aggregates", Max-Planck-Institut für Kolloid-und, Germany, 1 page.
Maldotti, A. et al., "Immobilization of $(n-Bu_4N)_4W_{10}O_{32}$ on Mesoporous MCM-41 and Amorphous Silicas for Photocatalytic Oxidation of Cycloalkanes with Molecular Oxygen", *Journal of Catalysis*, vol. 209, 2002, pp. 210-216.
Zhang, Q. et al., "Fe-MCM-41 for Selective Epoxidation of Styrene with Hydrogen Peroxide", *The Chemical Society of Japan*, Chemistry Letters 2001, pp. 946-947.
Melde, B.J. et al., "Mesoporous Sieves with Unified Hybrid Inorganic/Organic Frameworks", *Chem. Mater.*, vol. 11, No. 11, 1999, pp. 3302-3308.
Polarz, S. et al., "From Cyclodextrin Assemblies to Porous Materials by Silica Templating", *Angew. Chem. Int. Ed.*, vol. 40, No. 23, 2001, pp. 4417-4421.
Shi, D. et al., "Uniform Deposition of Ultrathin Polymer Films on the Surfaces of $Al_2O_3$ Nanoparticles by a Plasma Treatment", University of Cincinnati and University of Michigan, Jun. 2000, pp. 1-15.
Santra, S. et al., "Development of novel dye-doped silica nanoparticles for biomarker application", *Journal of Biomedical Optics*, vol. 6, No. 2, Apr. 2001, pp. 160-166.
Buchhammer, M. et al., "Nanoparticles based on polyelectrolyte complexes: effect of structure and net charge on the sorption capacity for solved organic molecules", *Colloid Polym. Sci.*, vol. 278, 2000, pp. 841-847.
Brunauer, S. et al., "Adsorption of Gases in Multimolecular Layers", *The Journal of the American Chemical Society*, vol. 60, Feb. 1938, pp. 309-319.
Schaber, P.M. et al., "Study of the urea thermal decomposition (pyrolsis) reaction and importance to cyanuric acid production", *American Laboratory*, Aug. 1999, pp. 13-21.
Bergna, H.E., Editor, "Silanol Groups, Siloxane Bridges, and Physically Adsorbed Water", The Colloid Chemistry of Silica, American Chemical Society 200th National Meeting, Aug. 26-31, 1990, pp. 22-23 and pp. 52-59.
Schweigert, I.V. et al., "Structure and properties of silica nanoclusters at high temperatures", *The American Physical Society*, Physical Review B, vol. 65, No. 235410, pp. 1-9.
Biermann, C.J. et al., Grafting of Poly(ethylenimine) onto Mesylated Cellulose Acetate, Poly(methyl methacrylate) and Poly-(vinyl chloride), *Carbohydrate Polymers*, vol. 12, 1990, pp. 323-327.
Yurieva, T.M. et al., Abstract of "Non-hyrdothermal synthesis of copper-, zinc- and copper-zinc hydrosilicates", *Materials Research Innovations*, vol. 5, No. 1, Jun. 2001, 2 pages.
Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.
Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.
Product Information Sheet for Snowtex®, 6 pages.
Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.
Article—*Ammonia vapour in the mouth as a diagnostic marker for Helicobacter pylori infection: preliminary "proof of principle" pharmacological investigations*, C. D. R. Dunn, M. Black, D.C. Cowell, C. Penault, N. M. Ratcliffe, R. Spence, and C. Teare, British Journal of Biomedical Science, vol. 58, 2001, pp. 66-76.
Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—*Validation of[13] C-Urea Breath Test for Diagnosis of Helicobacter Pylori Infection in the Singapore Population*, T. S. Chua, K. M. Fock, E. K. Teo, T. M. Ng, Singapore Medical Journal, vol. 43, No. 8, 2002, pp. 408-411.
Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.
Article—*Spectrophotometric Assay of Thiols*, Peter C. Jocelyn, Methods in Enzymology, vol. 142, 1987, pp. 44-67.
Abstract of Japanese Patent No. 7256025, Oct. 9, 1995.
PCT Search Report for PCT/US03/32846, Jun. 7, 2004.
Article—*Immunization of mice with peptomers covalently couopled to aluminum oxide nanoparticles*, Andreas Frey, Nicholas Manis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
Abstract of SU834073, May 30, 1981.
PCT Search Report and Written Opinion for PCT/US2004/011596, Aug. 30, 2004.
PCT Search Report and Written Opinion for PCT/US2004/016933, Nov. 2, 2004.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.

* cited by examiner

DURABLE CHARGED PARTICLE COATINGS AND MATERIALS

BACKGROUND OF THE INVENTION

This invention concerns coatings of charged particles onto substrates and methods of applying them.

The coating of charged particles onto substrates has not been well-explored, nor has it been used widely in commercial applications. The bonding of negatively charged particles to substrates has historically been quite difficult as the substrates are generally also negatively charged. Electrostatic repulsion forces resulted in coatings that were less than optimal and that lacked durability. The overcoming of this adhesion barrier would be a significant improvement in the ability to produce and the quality of, charged particle coatings for substrates.

SUMMARY OF THE INVENTION

In response to the difficulties and problems encountered in the prior art, new coatings and methods for coating have been developed for substrates. The coatings have high surface area particles that adhere to the substrates.

The ability to produce charged particles with functionalized surfaces and bind them to substrates creates the possibility of producing new products in numerous areas, such as in odor absorption, surface catalysis, chemical warfare agent absorption and the like.

The invention includes a substrate coating having a high surface area material and at least one metal ion adsorbed onto the high surface area material, durably coated onto a surface of a substrate. The high surface area material and the metal ion are capable of binding at least one like gaseous compounds, odorous compound, and combinations thereof. The substrate may be used in an item like odor removing wipes, protective barrier clothing, air filters, printing substrates, face masks, storage and garbage bags, refrigerator liners, auto headliners, dryer sheets, and deodorizing T-shirts.

The invention may be a durably coated fabric made from a fibrous substrate, a binder, and charged nanoparticles. It may also be a fabric made from fibers and sequentially deposited positively charged nanoparticles and negatively charged nanoparticles. The invention may be a substrate with a nanoparticle coating that has been durably attached to the substrate by ultrasonic energy. In another embodiment the invention may be a cellulosic fabric with nanoparticles where the nanoparticles have been added to the fabric in a wet-end addition.

Methods for practicing the invention include mixing high surface area particles with a binder to produce a solution, saturating a fabric in the solution, removing the fabric and drying the fabric. It includes the method of dipping a fabric in an aqueous mixture of high surface area particles, drying the fabric, dipping the fabric in a binder solution, and drying the fabric. It includes the method of dipping the fabric in an aqueous first mixture of high surface area particles, drying the fabric, dipping the fabric in second mixture of high surface area particles, and drying the fabric. It includes the method of dipping the substrate in an aqueous mixture of high surface area particles while simultaneously exposing the substrate to ultrasonic energy.

DETAILED DESCRIPTION

Figure 1:
FIG. 1 is a drawing of a nonwoven fabric

The invention concerns coatings that have absorbing, high surface area materials, such as nanoparticles, modified with at least one metal ion, as well as substrates that are durably coated with such coatings. While the invention will be described hereinafter with particular reference to nanoparticles, it will be understood that the invention is useful with various high surface area materials. A number of different processes may be used to durably attach the modified high surface area materials to the substrate. The modified high surface area materials of this invention are useful in removing gaseous compounds and/or odorous compounds.

"Gaseous compound" or "gas" includes any molecule or compound that can exist as a gas or vapor. This includes irritating agents like, for example, those used in chemical warfare agents or malodors found in the household environment. "Odorous compound" or "odor" refers to any molecule or compound detectable to the olfactory system.

Durably coated means that the coating having the high surface area materials remains on the substrate for a longer time than it otherwise would have, but for the inventive process of applying the materials. Durability is therefore a relative test. This requires the preparation of a standard base substrate prepared by dipping a substrate into an aqueous solution of high surface area materials, nipping it to remove excess liquid and drying it. Virtually any test may subsequently be used for durability, but it is important that both substrates be tested in the same manner. When performing any test, it is important that the high surface area materials falling from the substrate be measured, and not the separation of individual fibers. The loss of individual fibers may mean that the high surface area materials remained tightly bound to the substrate but that the substrate was weak. Possible tests for durability include the crocking colorfast test, the Taber abrasion test, gravimetric testing, airstream exposure and elemental analysis, the 30 second clean room standard testing protocol and a liquid wash followed by a light scattering test.

The substrates suitable for use in the practice of the invention include films, woven fabrics and nonwoven fabrics.

Film may be made by any one of a variety of film forming processes known in the art such as, for example, by using either cast or blown film equipment. In the case of a multilayer film, the layers are desirably simultaneously made such as, for example, forming by co-extrusion as disclosed in U.S. Pat. Nos. 4,522,203, 4,494,629 and 4,734,324. Examples of breathable barrier films suitable for use with the present invention are described in U.S. Pat. Nos. 5,695,868, 6,309,736, 6,075,179, and 6,111,163. Such films, prior to stretching, desirably have a basis weight of less than about 100 $g/m^2$ and even more desirably less than about 60 $g/m^2$. Upon stretching, multilayer films desirably have a basis weight of less than 60 $g/m^2$ and even more desirably between about 15 and 35 $g/m^2$.

"Fabric" means woven and nonwoven webs including, but not limited to webs such as tissues, towels, coform materials and fabric for clothing, furniture, vehicle, filtration and other applications. Fabrics may be made from cellulosic materials, cotton, polyesters, nylons, polyolefins, silk, and so forth, as well as combinations thereof. The majority of fabrics, particularly those made from cellulosic materials, tend to have negative electrical charges, i.e. negative streaming potential.

"Clothing" is used herein in a broad sense and includes applications in medical care, military and police attire, sporting goods applications as well as casual, everyday clothing.

A nonwoven fabric is a structure of individual fibers or threads which are interlaid, but not in an identifiable manner as in a woven or knitted fabric. Nonwoven fabrics or webs have been formed from many processes such as, for example, meltblowing processes, spunbonding processes, airlaying and bonded carded web processes as described in more detail below. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

Figure 2:
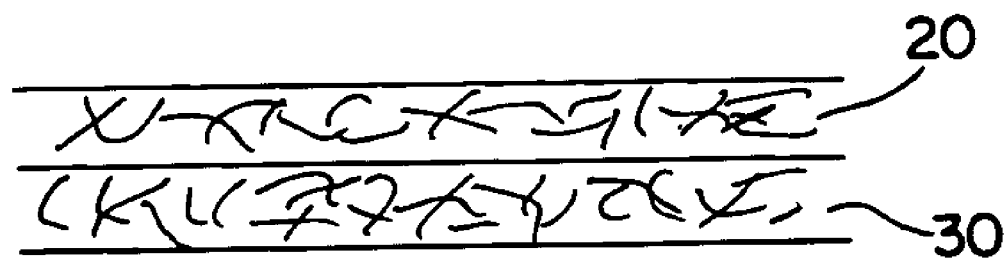
FIG. 2 shows a multilayer nonwoven laminate.

A nonwoven fabric may comprise, in reference to FIG. 1, fibers 10. The nonwoven fabric may be a multilayer nonwoven laminate as shown in FIG. 2, showing layers 20 and 30 made from fabrics produced by different processes. Multilayer laminates generally may have a number of nonwoven layers in many different configurations and may include other materials like films. Laminates of breathable films and nonwoven fabrics also are considered to be within the teachings of this invention provided at least one of the layers contains absorbing, high surface area materials.

A nonwoven fabric may be made according to processes like spunbonding, meltblowing, airlaying, bonding and carding, and so forth. Nonwoven fabrics may be made from thermoplastic resins including, but not limited to polyesters, nylons, and polyolefins. Olefins include ethylene, propylene, butylenes, isoprene and so forth, as well as combinations thereof.

The term "fibers" means small diameter fibers having an average diameter not greater than about 75 microns, for example, having an average diameter of from about 0.5 microns to about 50 microns, or more desirably, fibers may have an average diameter of from about 2 microns to about 40 microns.

"Spunbonded fibers" are small diameter fibers which are formed by extruding molten thermoplastic material as filaments from a plurality of fine, usually circular capillaries of a spinneret with the diameter of the extruded filaments then being rapidly reduced as described in, for example, U.S. Pat. No. 4,340,563 to Appel et al., and U.S. Pat. No. 3,692,618 to Dorschner et al., U.S. Pat. No. 3,802,817 to Matsuki et at., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more desirably, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, natural polymers (for example, rayon or cotton fibers) and/or synthetic polymers (for example, polypropylene or polyester) fibers, for example, where the fibers may be of staple length. Coform processes are described in commonly assigned U.S. Pat. No. 4,818,464 to Lau and U.S. Pat. No. 4,100,324 to Anderson et al. Webs produced by the coform process are generally referred to as coform materials.

A bonded carded web is made from staple fibers which are sent through a combing or carding unit, which breaks apart and aligns the staple fibers in the machine direction to form a generally machine direction-oriented fibrous nonwoven web. Once the web is formed, it then is bonded by one or more of several methods such as powder bonding, pattern bonding, through air bonding or ultrasonic bonding.

In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another. Examples of airlaid teachings include the DanWeb process as described in U.S. Pat. No. 4,640,810 Laursen et al. and assigned to Scan Web of North America Inc, the Kroyer process as described in U.S. Pat. No. 4,494,278 Kroyer et al. and U.S. Pat. No. 5,527,171 Soerensen assigned to Niro Separation a/s, the method of U.S. Pat. No. 4,375,448 Appel et al assigned to Kimberly-Clark Corporation, or other similar methods.

Multilayer nonwoven laminates are disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt a first fabric layer, e.g. a spunbond layer, then at least a second fabric layer, e.g. a meltblown layer. Additional layers may be added as desired in a like manner. Alternatively, the fabric layers may be made individually, collected in rolls, and combined in a separate bonding step. Such fabrics usually have a basis weight of from about 0.1 to 12 osy (6 to 400 gsm), or more desirably from about 0.75 to about 3 osy.

Nonwoven fabrics may further be treated such as, for example, by embossing, hydroentangling, mechanically softening, printing or treated in another manner in order to achieve desired aesthetics or other characteristics.

Gas and/or odor removing particles of this invention are modified high surface area materials. High surface area materials useful in this invention have a large surface area due to the small size of the individual particles of the high surface area material. High surface area materials useful in this invention have a suitable surface area of at least about 50 square meters/gram, suitably at least about 100 square meters/gram, and more suitably at least about 200 square meters/gram, and still more suitably at least about 500 square meters/gram or more.

Nanoparticles are examples of high surface area materials. "Nanoparticle" refers to a high surface material having a particle diameter of less than about 500 nanometers. The nanoparticles used in the practice of this invention act as carriers for at least one metal ion present on the surface of the nanoparticle, and the metal ion creates an active site that binds with at least one gaseous compound and/or odorous compound thereby removing the compound from the surrounding environment. Nanoparticles can also absorb certain gaseous compounds and/or odorous compounds from the surrounding environment by adsorption directly onto the surface of the nanoparticles. Silica nanoparticles modified by copper ions or alternatively, by silver ions, for example, were demonstrated to be effective in removing amine and sulfur based classes of odorous compounds.

Nanoparticles useful in this invention include silica, alumina, magnesium oxide, titanium dioxide, iron oxide, gold, zinc oxide, copper oxide, organic nanoparticles such as polystyrene, and combinations thereof. Nanoparticles are not generally ionic yet still have an overall electric Zeta Potential. "Zeta Potential" refers to the electrical potential, or electrokinetic potential, that exists across the interface of all solids and liquids. Naturally occurring chemical reactions on the surface of a nanoparticle result in the Zeta Potential of that nanoparticle and nanoparticles may have either positive or negative Zeta Potentials. Silica nanoparticles, for example, are tetrahedral complexes of silicon dioxide molecules. On the surface of the silica particles the silicon dioxide molecules can undergo chemical reactions forming silanol groups (SiOH) which react with other silanol groups to form siloxane bonds (Si—O—Si bonds). The dehydration reactions of the silanol groups to form the silanol bond and the reverse reactions result in a negative Zeta Potential and allow positively charged metal ions to adsorb onto the silica.

The nanoparticles useful in this invention will typically have a first Zeta Potential and a second Zeta Potential after adsorption of the metal ion onto the nanoparticle due to the addition of the oppositely-charged metal ions. The Zeta Potential change of the nanoparticle is related to the quantity of metal ions adsorbed onto the nanoparticle. This relationship provides a measurement for determining the amount of adsorbed metal ions and a method for controlling the amount of adsorption. For instance, the addition of a dilute solution of copper chloride drop-wise to a silica nanoparticle solution until the Zeta Potential of the silica suspension changed from −25 millivolts to a higher Zeta Potential, such as in the range of about −5 millivolts to −15 millivolts, was found to provide a sufficient concentration of metal ions adsorbed onto the nanoparticles to remove particular odorous compounds. The nanoparticle may have a difference between the first and second Zeta Potential of at least about 1.0 millivolt and suitably at least about 5.0 millivolts.

The nanoparticles are modified with metal ions that bond with compounds such as gases and odorous compounds. "Metal ion" refers to salt ions and/or ion complexes of transition metal elements designated as IB through VIIIB on the periodic table. Other ions can be used in the invention as well. Metal ions are adsorbed onto high surface area materials due to differences in electric potential. Positively charged metal ions are adsorbed onto a negatively charged surface of a nanoparticle and vice versa. Examples of metal ions useful in this invention include, without limitation, copper ion ($Cu^{+2}$), silver ion ($Ag^{+1}$), gold ion ($Au^{+1}$ and $Au^{+3}$), iron (II) ion ($Fe^{+2}$), iron (III) ion ($Fe^{+3}$), permanganate ion ($MnO_4^{-1}$), and combinations thereof.

The nanoparticle may have a negative Zeta Potential and adsorb positively charged metal ions. One suitable nanoparticle has a negative Zeta Potential of about −1 to −50 millivolts and suitably about −1 to −20 millivolts and is a silica nanoparticle. A number of silica nanoparticles useful in this invention are available from Nissan Chemical America Corporation, (Houston, Tex., USA) under the tradename SNOWTEX® and have a particle size range of 1–100 nanometers. The silica nanoparticle can be modified with a positively charged metal ion such as copper ions, silver ions, gold ions, iron ions, and combinations thereof. More information on SNOWTEX® particles may be found at www.snowtex.com.

Yet another useful nanoparticle has a positive Zeta Potential and adsorbs negatively charged metal ion complexes. One suitable nanoparticle has a positive first Zeta Potential of about 1 to 70 millivolts and suitably about 10 to 40 millivolts and may be an alumina nanoparticle. Alumina nanoparticles are available from Nissan Chemical under the tradename ALUMINASOL®, and have a size range of about 1–300 nanometers. Another alumina coated silica nanoparticle having a positive Zeta Potential is available from Nissan Chemical under the tradename SNOWTEX® AK. The alumina nanoparticle can adsorb negatively charged metal ions and metal ion complexes such as permanganate ions.

It is also possible to bond metal and silica particles to form a "coordinate" and/or "covalent bond." This may have a variety of benefits, such as reducing the likelihood that any of the metal will remain free during use (e.g., after washing). Strong adherence of the metal to the silica particles, further, also optimizes odor adsorption effectiveness. Numerous techniques may be utilized to form a stronger bond between the transition metal and silica particles. Silica sols, for example, are generally considered stable at a pH of greater than about 7, and particularly between a pH of 9–10. When dissolved in water, salts of transition metals are acidic (e.g., copper chloride has a pH of approximately 4.8). Thus, when such an acidic transition metal salt is mixed with a basic silica sol, the pH is lowered and the metal salt precipitates on the surface of the silica particles. This compromises the stability of the silica particles. Further, at lower pH values, the number of silanol groups present on the surface of the silica particles is reduced. Because the transition metal binds to these silanol groups, the capacity of the particles for the transition metal is lowered at lower pH values. In order to ameliorate the pH-lowering affect caused by the addition of an acidic transition metal salt (e.g., copper chloride), certain embodiments of the present invention employ selective control over the pH of the silica particles during mixing with the transition metal. The selective control over pH may be accomplished using any of a variety of well-known buffering systems known in the art.

The use of pH control in the modification of silica nanoparticles was demonstrated using a 10 weight percent suspension of SNOWTEX-OXS® nanoparticles having an unmodified particle size of 4 to 6 nm. The pH of the solution was adjusted to 8.7 and then added to a solution of copper chloride with high mixing shear (about 10,000 rpm). The pH, Zeta potential and particle size were monitored and when a positive Zeta potential was obtained the addition of copper chloride was stopped. The resulting copper modified nanoparticle had a particle size of about 43 nm and a surface area of about 500 square meters per gram.

Other techniques may also be utilized to further enhance the strength of the bonds formed between the transition metal and the silica particles. Coupling agents in an effective amount may be used to link the transition metal to the silica particle, for example. Such coupling agents may be employed with or without the pH adjustment discussed above. In some cases, an organofunctional silane coupling agent may be used to link the transition metal to the silica particles. Some examples of suitable organofunctional silane coupling agents that may be used include, but are not limited to, vinyltrichlorosilane, vinyltrimethoxysilane, vinyltriethoxysilane, vinylmethyldichlorosilane, vinylmethyldimethoxysilane, vinylmethyldiethoxysilane, 5-hexenyltrimethoxysilane, 3-glycidoxypropyltrimethoxysilane, 3-glycidoxypropyltriethoxysilane, 3-glycidoxypropylmethyldimethoxysilane, 3-glycidoxypropylmethyldiethoxysilane, 3-(meth)acryloxypropyltrimethoxysilane, 3-(meth)acryloxypropyltriethoxysilane, 3-(meth)acryloxypropylmethyldimethoxysilane, 3-(meth)acryloxypropylmethyldiethoxysilane, 4-vinylphenyltrimethoxysilane, 3-(4-vinylphenyl)propyltrimethoxysilane, 4-vinylphenylmethyltrimethoxysilane, 3-aminopropyltrimethoxysilane, 3-aminopropyltriethoxysilane, 3-aminopropylmethyldimethoxysilane, 3-aminopropylmethyldiethoxysilane, 3-(2-aminoethyl)aminopropyltrimethoxysilane, 3-mercaptopropyltrimethoxysilane, 3-mercaptopropyltriethoxysilane, 3-mercaptopropylmethyldimethoxysilane, 3-mercaptopropylmethyldiethoxysilane, and partial hydrolyzates thereof. Of these coupling agents, organofunctional alkoxysilanes, and particularly aminofunctional alkoxysilanes (e.g., 3-aminopropyltriethyoxysilane), are preferred.

Generally speaking, the silane coupling agents may be covalently linked to the silica particles through the silanol groups (Si—OH) present on the surface thereof. Specifically, the silicon atom of the silane coupling agent may form a covalent bond with the oxygen of the silanol group. Once the silane coupling agent is covalently linked to the silica particles, the organofunctional group may form a coordinate bond with the transition metal. Copper, for example, may form a coordinate bond with different amino groups present on aminopropyltriethoxysilane coupling agents.

The addition of a metal ion adsorbed onto the surface of a nanoparticle provides an active site for capturing and neutralizing gases and odorous compounds. In addition, modified nanoparticles still have a large surface area that is useful in absorbing other odorous compounds. The metal ion active sites of the modified nanoparticles are useful in removing odorous compound such as mercaptans, ammonia, amines, mono- and di-sulfides, and hydrogen sulfide. Other odorous compounds such as aliphatic ketones, carboxylic acids, aliphatic aldehydes, and aliphatic terpenoids can be removed by adsorption onto the large surface area of the modified nanoparticles. Modified nanoparticles are useful in removing odors caused by sulfides, disulfides, trisulfides, thiols, mercaptans, ammonia, amines, isovaleric acid, acetic acid, propionic acid, hexanal, heptanal, 2-butanone, 2-pentanone, 4-heptanone, and combinations thereof. Modified nanoparticles can also remove gases such as ethylene gas, carvone, dienals, and terpenoids.

More than one type of metal ion can be coated on a nanoparticle. This has an advantage in that certain metal ions may be more effective at removing specific gases and/or odorous compounds than other metal ions. More than one type of metal ion may be adsorbed onto a nanoparticle for more effectively removing more than one type of gaseous compound or odorous compound from a medium or for removing at least one gaseous compound and at least one odorous compound from a medium. The use of two or more different modified nanoparticles in combination can remove numerous odorous compounds. Modified silica nanoparticles, for example, are useful for removing sulfur containing compounds and amine odors and modified magnesium oxide nanoparticles are useful in removing carboxylic acid odors. Combining modified nanoparticles allows for removal of a broader range of odors.

Modified nanoparticles are made by mixing nanoparticles with solutions containing metal ions. Such solutions are generally made by dissolving metallic compounds into a solvent, resulting in free metal ions in the solution. The metal ions are drawn to and adsorbed onto the nanoparticles due to the electric potential differences. The Zeta Potential of a nanoparticle changes after the adsorption of metal ions and so the Zeta Potential can be used to monitor the adsorption of metal ions onto the nanoparticle.

Further discussion of the modification of nanoparticles may be found in U.S. patent application Ser. No. 10/137,052, filed on Apr. 30, 2002, which is incorporated by reference.

The high surface area materials used in the practice of the invention may be added to a substrate in an amount between about 0.01 and 20 weight percent, desirably between about 0.1 and 10 weight percent, more desirably between 0.5 and 5 weight percent.

Binders are used in certain aspects of the invention as discussed below. The binder may be, for example, a KYMENE® binder (from Hercules Industries, Inc., Wilmington, Del., USA) or polyethyleneimine (from Polysciences, Inc., of Warrington, Pa., USA or Aldrich Chemical Company, Milwaukee, Wis., USA,) and similar materials. The amount of binder is desirably between about 0.01 and 5 weight percent.

Substrates having gas and odor absorbing, high surface area materials are suitable for use in many commercial articles like, for example, personal care products, odor removing wipes, protective barrier clothing, air filters, printing substrates, face masks, storage and garbage bags, refrigerator liners, auto headliners, dryer sheets, deodorizing T-shirts and so forth.

"Personal care product" means diapers, training pants, absorbent underpants, adult incontinence products, and feminine hygiene products.

Figure 3:
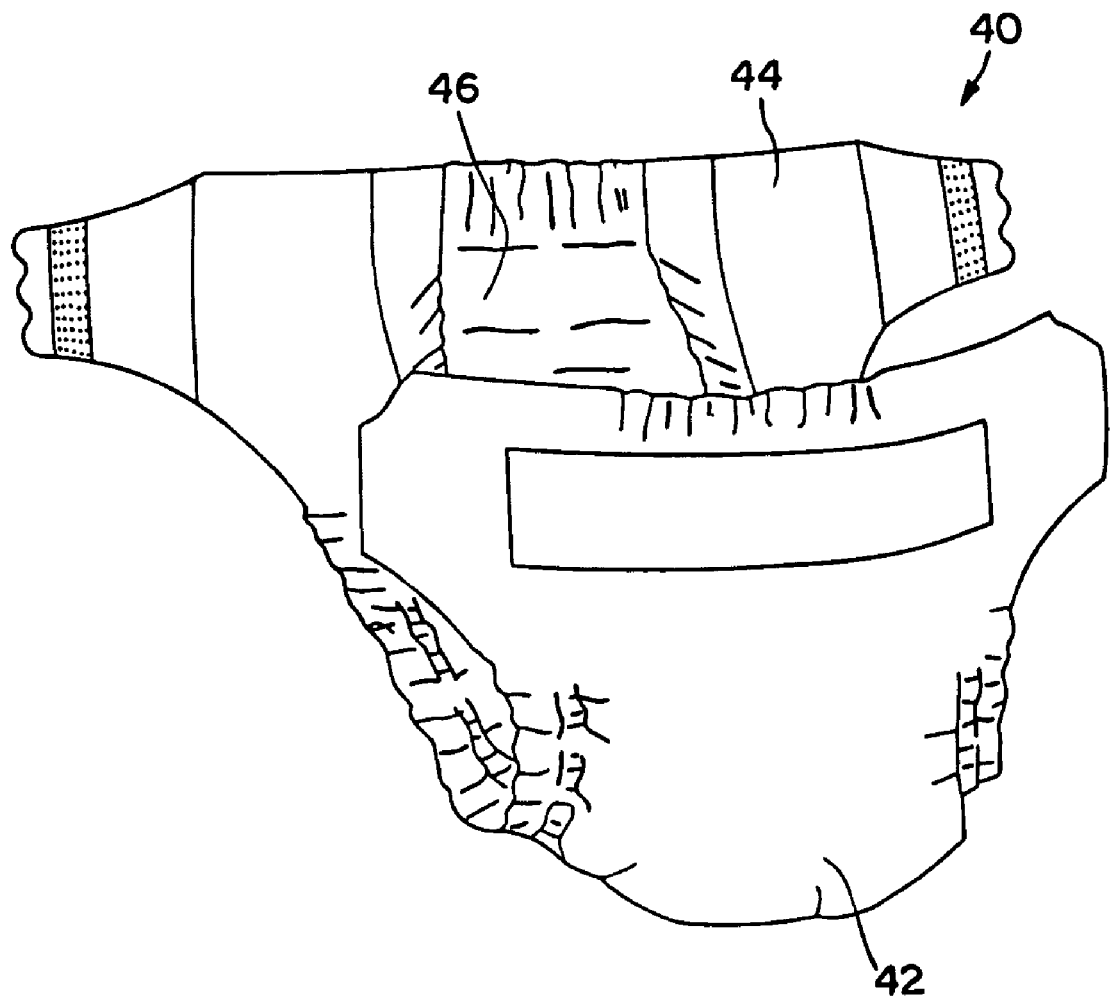
FIG. 3 is a drawing of a diaper in a partially opened view.
Figure 4:
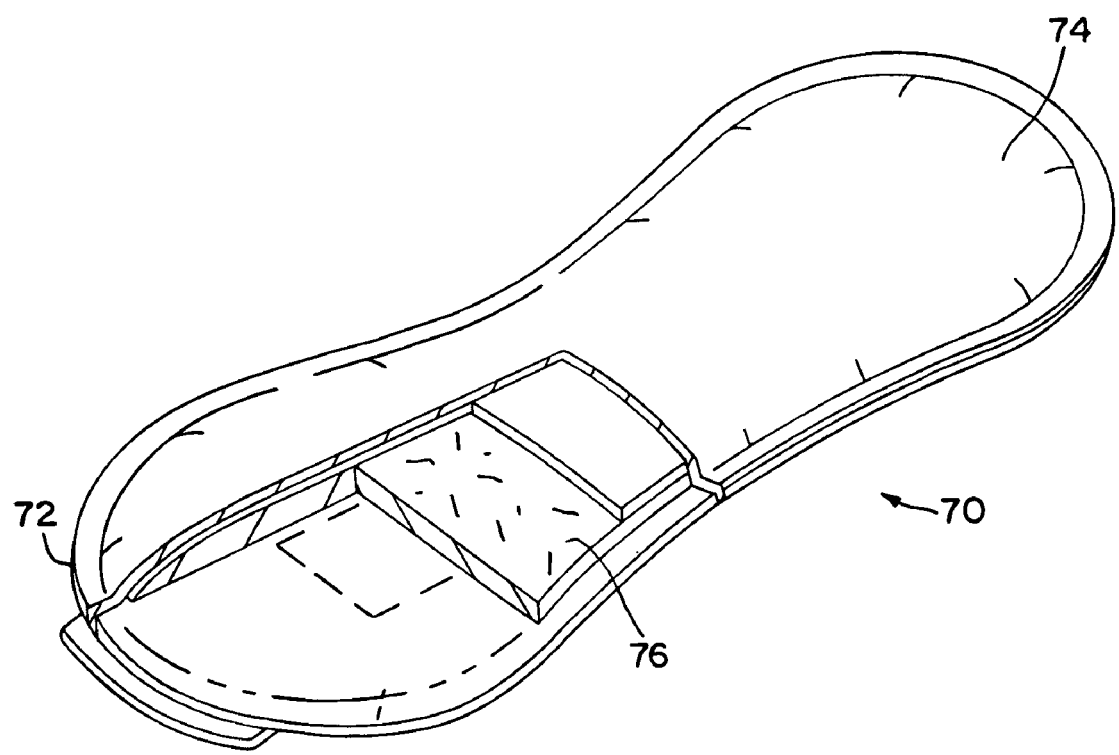
FIG. 4 is a drawing of a feminine hygiene pad.

Personal care products generally include an outer cover which is the most exterior layer, a liner which goes against the wearer, and may also contain other layers and materials between them, such as, for example, absorbent structures that are typically made with superabsorbents and cellulosic materials. The outer cover functions to prevent body exudates contained in an absorbent structure from wetting or soiling the wearer's clothing, bedding, or other materials contacting the product. The outer cover may be, for example, a polyethylene film or a woven or nonwoven fabric. The liner serves to isolate the wearer's skin from the liquids held in an absorbent structure and should be compliant, soft feeling and non-irritating. Liners are commonly nonwoven fabrics made, for example, from spunbond polypropylene. FIG. 3 s a drawing of a diaper 40 showing the outer cover 42, the liner 44 and the absorbent structure 46. FIG. 4 shows a feminine hygiene pad 70 having an outer cover 72, liner 74 and absorbent structure 76.

In another aspect of this invention, the substrate having the durable coating is used to absorb gases that plants produce to ripen fruit. Ethylene gas is produced by plants as a hormone to aid fruit ripening. Removing ethylene gas as it is produced can slow and control the fruit ripening process. Permanganate ion modified alumina nanoparticles are useful in removing ethylene gas and such nanoparticles may be added to breathable films, nonwoven fabrics or multilayer laminates using the methods described above. The substrate can then be used in packaging and storing fruit to inhibit ripening by removing ethylene gas.

Figure 5:
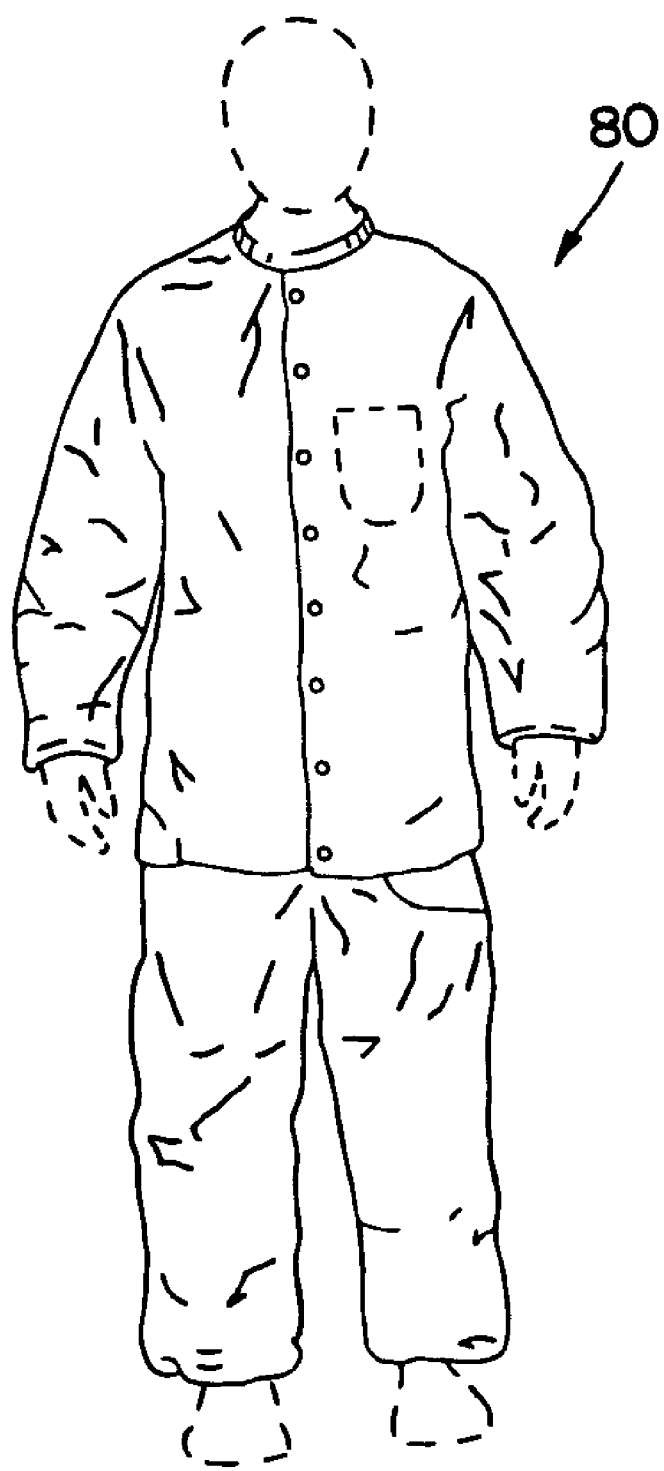
FIG. 5 shows a drawing of a soldier wearing an absorbent, light-weight, chemical protective suit.

Protective barrier clothing includes clothing used in any application where protection from airborne chemical agents is important, since many chemically irritating moieties act in the same manner as odor containing chemicals and so may be rapidly absorbed and neutralized by the coatings and substrates of this invention. In another aspect the substrate is used to produce clothing for protection against chemical warfare agents. FIG. 5 shows a drawing of a soldier wearing an absorbent, light-weight, chemical protective suit 80. Airborne chemical agents designed to irritate the body may be absorbed by the high surface area material-coated substrates of the invention.

The absorbing, high surface area materials of this invention may be added to substrates in a number of ways. The substrate may be dipped into a solution containing high surface area materials, removed from the bath, and either dried or passed through a nip to remove excess solution and then dried. The treated substrate may then be dipped in a second solution containing a binder and dried. The binder causes the charged particles to remain on the fiber despite electrostatic forces to the contrary. The binder may alternatively be added to the high surface area material solution prior to the first dip, thus allowing for only one dip and nip step.

Alternatively, since positively charged particles like, for example, SNOWTEX-AK® nanoparticles from Nissan Chemical are believed to adhere to negatively charged fibers, a fabric substrate containing negatively charged fibers may be treated with a solution of positively charged nanoparticles and allowed to dry. The dried substrate may be subsequently treated with a solution of negatively charged nanoparticles like, for example, SNOWTEX-PS® nanoparticles from Nissan Chemical. The negatively charged particles will adhere to the positively charged particles which in turn adhere to the negatively charged substrate, resulting in the desired addition of particles. A binder is optional in this aspect and may be added to either nanoparticle solution or as a separate step after the second nanoparticle addition.

In yet another alternative, the substrate, in the presence of the odor absorbing, high surface area materials, is exposed to ultrasonic energy. It is believed, though the inventors do not wish to be bound by this belief, that ultrasonic energy introduced to an aqueous solution of the high surface area materials will cause a change in the temperature and pressure of the solution in the micro-environment at the tip of the ultrasonic horn. This change causes the high surface area materials to adhere durably to the substrate. This method is well suited for use with polymeric nonwoven fabrics, which, while having a weak negative charge, tend to be highly hydrophobic, thus making less aggressive treatment methods less effective on such substrates. The introduction of ultrasonic energy to the aqueous solution and substrate appears to overcome the natural hydrophobicity of the polymeric substrates. The energy requirement for this method, at laboratory scale, is generally between 1 and 10 kilowatts, more desirably between 1.5 and 5 kilowatts, and most desirably about 2 kilowatts as measured by the output of the ultrasonic unit.

Ultrasonic bonding has been used previously as a method of bonding two or more materials by passing the materials between a sonic horn and anvil roll in air, as described in U.S. Pat. No. 4,374,888 to Bornslaeger. The inventors have found, however, that a substrate may be immersed in a high surface area material solution into which may be submerged the horn of an ultrasonic bonding machine and that this can cause the aqueous solution to wet the usually hydrophobic fibers and to cause suspended or dissolved materials (e.g. the high surface area materials) to be deposited onto the surface of the fibers. Unlike in air, which is highly compressible, the aqueous solution in which the horn and substrate are immersed transmits the sonic energy efficiently from the horn to the adjacent substrate. The solution of high surface area materials may also contain a binder.

Figure 6:
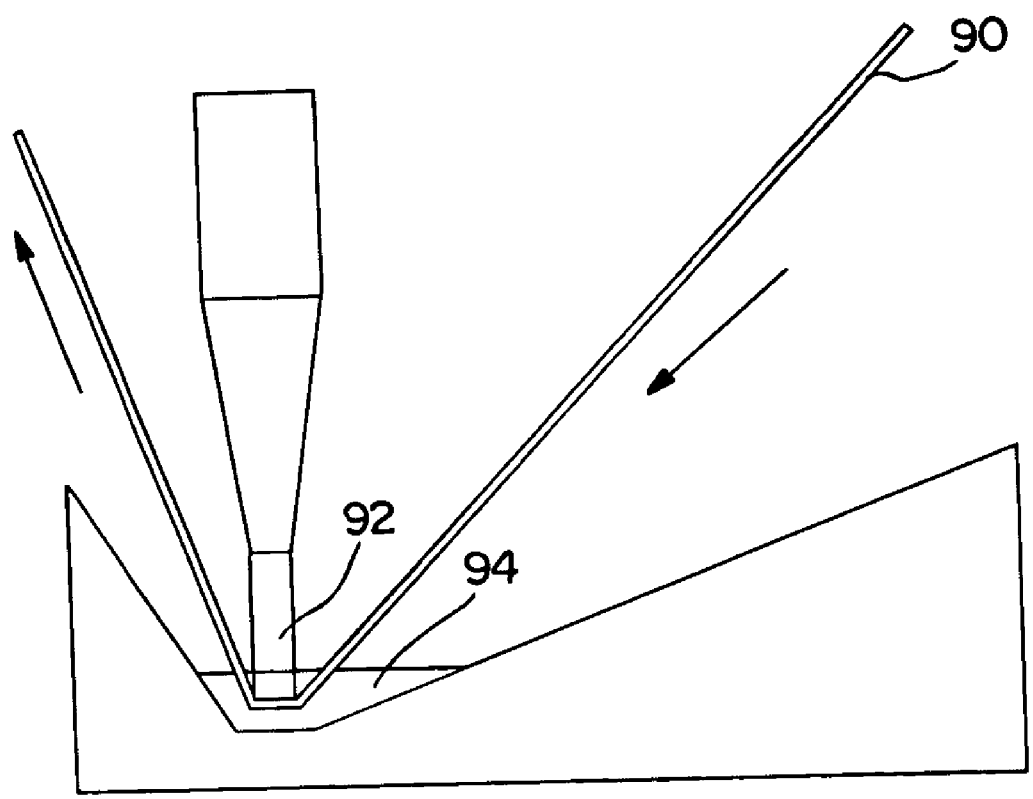
FIG. 6 is a diagram of a fabric being exposed to ultrasonic energy while within an aqueous solution.

FIG. 6 is a diagram of a fabric being exposed to ultrasonic energy while within a bath of aqueous high surface area material. The fabric 90 moves in the direction of the arrows and passes next to the end of the ultrasonic horn 92 while the horn 92 is immersed in the solution 94. The fabric 90 moves away from the horn 92 to storage, not shown. Manufactures of suitable ultrasonic equipment include Branson Ultrasonic Corporation, Applied Technology Group, Danbury, Conn., USA, UE Systems Inc. of Elmsford, N.Y., USA, Mecasonic SA of Chatou, France, and Dukane Corporation, St. Charles, Ill., USA.

In yet another method, the nanoparticles may be added, with or without a binder, to the "wet-end" of a cellulosic substrate process like, for example, paper making. In this method, the particles are added to a large container having an aqueous suspension of fibers from plant sources like trees. The fibers are conventionally wet-laid upon a forming sheet and moisture is removed, thus forming the cellulosic sheet. The sheet may be a tissue, paper, and the like. Sheets thus produced have a durable coating of nanoparticles.

The following examples aid in the understanding of the invention.

EXAMPLE 1

Base sheet preparation: A dilute suspension of modified silica nanoparticles was made by adding SNOWTEX-AK® nanoparticles from Nissan Chemical to deionized water to produce a 2 weight percent solution. A solution of 5 weight percent copper chloride ($CuCl_2$) from Aldrich Chemical in an amount of 120 milliliters was added to 1120 ml of the 2 weight percent nanoparticle solution. Approximately 28.75 grams of Acid Blue 45, also from Aldrich Chemical was added to the above solution. A SCOTT® paper towel from Scott Paper Company of Mississauga, Ontario, Canada, was coated with the solution by dipping and allowed to dry in air at room temperature to produce an odor control sheet. Durable coating: A solution containing 1 weight percent KYMENE® 625 LX binder from Hercules Incorporated, Wilmington, Del., USA, was prepared. The base sheet was dipped in the KYMENE® binder solution, passed through a nip to remove excess liquid and cured at 80° C. for one hour.

Durability Testing: Five repetitions of each sample of odor control base sheet and KYMENE® binder treated sheet were tested according to the 30 second clean room standard testing protocol.

The 30 second clean room protocol is carried out in a room that meets class 100 clean room quality or better. A 23 cm by 23 cm sample is clamped between two holders that have a flexing stroke of 119.8 mm with a twist of 180 degrees at a rate of 60 cycles/minute. The stroke is affixed to the base of a Gelbo Flex unit, available from US Testing Co., Inc. of Hoboken, N.J., USA. The Flex unit is enclosed in a 1 cubic foot (28317 $cm^3$) box. An airflow of 1 cubic foot per minute flows through the box to a laser particle counter as the test proceeds. Laser particle counters include Model 200 L from Met One, Inc., of Grants Pass, Oreg., USA and Model C1-7350 from Climet Instrument Co. of Redlands, Calif., USA. The results, in Table 1, show a dramatic decrease in the shedded particle counts after binder treatment, such as, for example, from 57,841 counts to 8557 counts for 0.5 micron size particles.

TABLE 1

| Particle Size | Particle Count | |
|---|---|---|
| | Base Sheet | Binder Treated Sheet |
| 10 microns | 100 | 108 |
| 5 microns | 417 | 174 |
| 1 micron | 18194 | 2465 |
| 0.7 microns | 35230 | 4813 |
| 0.5 microns | 57841 | 8557 |
| 0.3 microns | 78019 | 13362 |

EXAMPLE 2

Base sheet preparation: An odor control sheet was prepared in the same manner as in Example 1.

Durable coating: A solution containing 1 weight percent KYMENE® 625 LX binder from Hercules Incorporated, Wilmington, Del., USA, was prepared. The odor control sheet was dipped in the KYMENE® binder solution, passed through a nip to remove excess liquid and cured at 80° C. for one hour.

Durability Testing: Five repetitions of each sample of odor control base sheet and KYMENE® binder treated sheet were tested according to the 30 second clean room standard testing protocol. The results, in Table 2, show a dramatic decrease in the shedded particle counts after binder treatment, such as, for example, from 57,058 counts to 15,731 counts for 0.5 micron size particles.

TABLE 2

| Particle Size | Particle Count | |
|---|---|---|
| | Base Sheet | Binder Treated Sheet |
| 10 microns | 128 | 53 |
| 5 microns | 588 | 161 |
| 1 micron | 19357 | 4932 |
| 0.7 microns | 35598 | 9551 |
| 0.5 microns | 57058 | 15731 |
| 0.3 microns | 76558 | 21248 |

EXAMPLE 3

Base sheet preparation: An odor control sheet was prepared in the same manner as in Example 1.

Durable coating: A solution containing 1 weight percent branched polyethyleneimine (PEI) having a molecular weight of about 10,000, available from Polysciences Inc. of Warrington, Pa., USA, was prepared. The odor control sheet was dipped in the PEI binder solution, passed through a nip to remove excess liquid and cured at 80° C. for one hour.

Durability Testing: Five repetitions of each sample of odor control base sheet and PEI binder treated sheet were tested according to the 30 second clean room standard testing protocol described above. The results, in Table 3, show a dramatic decrease in the shedded particle counts after binder treatment, such as, for example, from 57,058 counts to 36,409 counts for 0.5 micron size particles.

TABLE 3

| Particle Size | Particle Count | |
|---|---|---|
| | Base Sheet | Binder Treated Sheet |
| 10 microns | 128 | 419 |
| 5 microns | 588 | 1056 |
| 1 micron | 19357 | 13985 |
| 0.7 microns | 35598 | 23898 |
| 0.5 microns | 57058 | 36409 |
| 0.3 microns | 76558 | 47430 |

The odor removing capability of the binder-treated sheets were tested for thiol odor removal using the GC headspace procedure with ethyl mercaptan (1 ul) as the odorant. This test uses a gas chromatography column, in this case a model DB-624:30 m, 0.25 mm ID, 1.4 micron film, catalog number 122 -1334, serial number 8847844, from J&W Scientific, Inc. of Folsom, Calif., USA. The GC unit was Agilent Technologoes 5890 GC with 7694 headspace analyzer with flame ionization detector. The headspace parameters were: oven temperature 37° C., loop temperature 85° C., transfer line temperature 90° C., GC cycle time 10 min., vial equalization time 10 min., pressurization time 0.2 min, loop fill time 0.2 min, injection time 0.3 min. The gas chromatographic parameters were: oven temperature 35° C. for five min., inlet temperature 105° C., detector temperature 225° C., and run time 5 minutes. Samples were weighted and place into the headspace vials without touching the bottom of the vial. The ethyl mercaptan was placed into the bottom of the vial using a microliter syringe. The vial was immediately crimped to seal in the gases. The amounts of odor for 20–200 percent odor removal by the sample were adjusted by dilution with hexane. The samples were prepared 10–60 minutes before running. Standard samples using the same amount of odor were run without a sample in the vial. Percent removal of odor was calculated by subtracting the area of the ordo remaining from the total odor area and dividing by the total odor area. Gas chromatographic analysis indicated that the thiol binding capability of the basesheet was not diminished significantly by the addition of the polymeric binder.

EXAMPLE 4

A dilute suspension of modified silica nanoparticles was made by adding SNOWTEX-O® nanoparticles from Nissan Chemical to deionized water to produce a 2 weight percent solution. A second solution was prepared by adding 132.5 mg of polyethyleneimine (PEI) (Polysciences Inc.) having a molecular weight of about 1800, to 110 ml of di-ionized water. A 0.5 ml amount of the PEI solution was added to 300 ml of the nanoparticle solution with the further addition of $CuCl_2$ (Aldrich Chemical) in a sufficient amount to make a 0.067 weight percent solution of $CuCl_2$.

A KLEENEX® paper towel was dipped in the resulting solution for 1 minute, passed through a nip to remove excess liquid and dried at room temperature.

Durability Testing: The treated KLEENEX® towel, and a KLEENEX® towel treated in a like manner but without PEI, were hung on a line and blown by an HT-800-19 series fan, manufactured by Honeywell of Southborough, Mass., USA at half speed for 24 hours. The fan-blown towels were analyzed by furnace elemental analysis to determine the silicon content before and after blowing. It was found by the analysis that the sample without PEI had lost about 9 percent of its Si content as a result of the fan blowing. The sample with PEI lost no silicon, indicating that the silica nanoparticles were well bonded to the towel. The odor removal capability was also tested and found to be essentially the same for each sample.

EXAMPLE 5

A dilute suspension of modified silica nanoparticles was made by adding SNOWTEX-O® nanoparticles from Nissan Chemical to deionized water to produce a 2 weight percent solution. $CuCl_2$ (Aldrich Chemical) in a sufficient amount to make a 60:1 mole ratio of copper ions to silica nanoparticles was added. A solution containing 1 weight percent KYMENE® 625 LX binder from Hercules Incorporated, Wilmington, Del., USA, was prepared. The nanoparticle/copper solution was added to the KYMENE® binder solution with vigorous stirring for 20 minutes. This solution was added to a solution containing 1 weight percent cellulose pulp fibers with vigorous stirring.

A sheet was formed by wet-laying the above solution and drying it at 100 C to produce a paper towel having a basis weight of 40 gsm. The add-on rate was determined to be 2 weight percent.

Durability Testing: The dried sheet was tested using the 24 hour fan blowing test described above in Example 4. No significant weight loss was detected by gravimetric analysis. The odor removal capability was also tested according to the GC headspace procedure described above in Example 3. Ethyl mercaptan was removed at a rate of 0.9 mg/g of sample for the inventive towel versus a rate of 0 mg/g for an untreated towel.

EXAMPLE 6

A dilute suspension of modified silica nanoparticles was made by adding SNOWTEX-AK® nanoparticles from Nissan Chemical to deionized water to produce a 5 weight percent solution. $CuCl_2$ (Aldrich Chemical) in a sufficient amount to make a 60:1 mole ratio of copper ions to silica nanoparticles was added. A piece of a polyester/cellulose wetlaid fabric from Ahlstrom Corporation of Windsor Locks, Conn., USA, and having a basis weight of 18.6 gsm, was dipped in the resulting solution for about 1 minute, passed through a nip to remove excess liquid and dried at room temperature. A second solution of SNOWTEX-PS® nanoparticles from Nissan Chemical was prepared, at a concentration of 2.5 weight percent, also having $CuCl_2$ (Aldrich Chemical) in a sufficient amount to make a 60:1 mole ratio of copper ions to silica nanoparticles. The cationically modified wetlaid fabric was dipped in the resulting (second) solution for 1 minute, passed through a nip to remove excess liquid and dried at room temperature. The add-on rate for the nanoparticles was 15.4 weight percent plus or minus 1.2 weight percent, with about 7.8 weight percent being from the first dip and the balance from the second.

Durability Testing: This has not been completed by the inventors believe that the treated sheet will show greater durability of the coating than a similar sheet with only a coating of SNOWTEX-PS® nanoparticles.

EXAMPLE 7

A dilute suspension of modified silica nanoparticles was made by adding a solution of 1 weight percent $CuCl_2$ (Aldrich Chemical) and a solutioni of 20 weight percent SNOWTEX-AK® nanoparticles (Nissan Chemical) to 850 ml deionized water in amounts according to Table 4 below. Note that the amounts of $CuCl_2$ and nanoparticles in Table 4 are in grams. Pieces of meltblown polypropylene nonwoven fabric having a basis weight of 35 gsm and measuring 3.5 inches by 30 inches (8.9 cm by 76.2 cm) were passed around the tip of an ultrasonic horn submerged in the solution. The ultrasonic horn was a 2000 watt Branson 920 iw bonder with a 0.5 by 6 inch (1.27 cm by 15.24 cm) horn and 1:1.5 booster, available from Branson Ultrasonics. Tension was maintained on the fabric by hand so it was sliding directly across the submerged horn face at a rate of either 1 or 3 inches per second (2.54 cm/s or 7.6 cm/s) as indicated in Table 4. After treatment, samples 3, 4, 6 and 8 were washed by immersion in 120 ml deionized water for about an hour in a sonic bath. No detectable changes in the weight of the samples was found after extraction, indicating a durable surface.

TABLE 4

35 gsm polypropylene meltblown fabric

| Sample | 1% CuCl2 grams | 20% Sn-AK grams | Rate in/sec. | g solid/ 850 mL | g solid/ 1 mL | Initial Mass (g) | wet add-on | dry add-on | treatment gsm |
|---|---|---|---|---|---|---|---|---|---|
| 1 | 107.5 | 50 | 1 | 11.075 | 0.01303 | 1.76 | 681% | 11.9% | 4.23 |
| 2 | 107.5 | 50 | 3 | 11.075 | 0.01303 | 1.72 | 620% | 12.8% | 4.43 |
| 3 | 107.5 | 50 | 1 | 11.075 | 0.01303 | 1.80 | 629% | 13.3% | 4.83 |
| 4 | 107.5 | 50 | 3 | 11.075 | 0.01303 | 1.66 | 603% | 11.4% | 3.82 |
| 5 | 5.4 | 50 | 3 | 10.054 | 0.01183 | 1.84 | 679% | 10.9% | 4.03 |
| 6 | 5.4 | 50 | 3 | 10.054 | 0.01183 | 1.61 | 703% | 8.1% | 2.62 |
| 7 (control) | 0 | 0 | 3 | 0 | 0.00000 | 1.73 | 507% | 1.2% | 0.40 |
| 8 (control) | 0 | 0 | 3 | 0 | 0.00000 | 1.69 | 409% | 0.0% | 0.00 |

EXAMPLE 8

A dilute suspension of modified silica nanoparticles was made by adding 3130 grams of a 20 weight percent SNOWTEX-O® nanoparticle solution to 390 mls of an 8 weight percent $FeCl_3$ solution. Approximately 850 ml of this suspension was used to immerse a film and the tip of the sonic horn of an ultrasonic machine. The film was a microporous calcium carbonate filled polyethylene film with a basis weight of 19 gsm. The film was was passed around an ultrasonic horn while submerged in the resulting solution at a rate of about 5 cm/s. The ultrasonic horn was a 2000 watt Branson 920iw bonder with a 0.5 by 6 inch (1.27 cm by 15.24 cm) horn and 1:1.5 booster, available from Branson Ultrasonics. Tension was maintained on the film by hand so it was sliding directly across the submerged horn face at a rate of about 2.54 cm/s. After treatment, some of the film was washed by immersion in deionized water for about an hour in a sonic bath.

The odor removal capability was tested according to the GC headspace procedure described above in Example 3. Ethyl mercaptan (2.4 ul) was the odorant and approximately 0.25 grams of film was used in each vial. A control film without nanoparticles removed about 18 percent of the ethyl mercaptan while the inventive coating removed about 45 percent of the ethyl mercaptan for unwashed samples and 53 percent for washed samples.

Durability Testing: An extractables study was performed on the treated film by immersing in water for 4 hours at 37° C. Thereafter, the water is analyzed by inductively coupled plasma, as is known in the art. No iron was found in this test, which had a detectible limit of 64 ppm.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A fibrous substrate comprising:
   nanoparticles having a surface area of at least about 50 square meters per gram, wherein the nanoparticles are modified with a metal ion and have a negative zeta potential prior to modification with the metal ion, and wherein the zeta potential of the modified nanoparticles is from about −5 millivolts to about −15 millivolts and is greater than the zeta potential of the nanoparticles prior to modification; and
   a binder that durably adheres the modified nanoparticles to the substrate.

2. The substrate of claim 1, wherein the negative zeta potential is from about −1 millivolt to about −50 millivolts.

3. The substrate of claim 1, wherein the metal ion is adsorbed onto a surface of the nanoparticles.

4. The substrate of claim 1, wherein the metal ion forms a coordinate or covalent bond with the nanoparticles.

5. The substrate of claim 1, wherein the nanoparticles have a surface area of at least about 100 square meters per gram.

6. The substrate of claim 1, wherein the nanoparticles have a size of less than about 500 nanometers.

7. The substrate of claim 1, wherein the nanoparticles comprise silica.

8. The substrate of claim 1, wherein the metal ion includes copper, silver, gold, iron, manganese, or combinations thereof.

9. The substrate of claim 1, wherein the substrate contains polyolefin fibers.

10. The substrate of claim 1, wherein the substrate is a spunbond web, meltblown web, or combination thereof.

11. The substrate of claim 1, wherein the substrate contains cellulosic fibers.

12. The substrate of claim 1, wherein the modified nanoparticles constitute from about 0.1 to about 10 wt.% of the substrate.

13. The substrate of claim 1, wherein the binder constitutes from about 0.01 to about 5 wt.% of the substrate.

14. A personal care product comprising the substrate of claim 1.

15. Protective barrier clothing comprising the substrate of claim 1.

16. The substrate of claim 1, wherein the nanoparticles and binder are sequentially applied to the substrate.

17. A fibrous substrate comprising:
   first nanoparticles having a surface area of at least about 50 square meters per gram, wherein the first nanoparticles are modified with a metal ion and have a negative zeta potential prior to modification with the metal ion; and
   second nanoparticles having a positive zeta potential that durably adhere the modified nanoparticles to the substrate.

18. The substrate of claim 17, wherein the second nanoparticles have a zeta potential of from about 1 millivolt to about 70 millivolts.

19. The substrate of claim 17, wherein the first nanoparticles have a zeta potential of from about −1 millivolt to about −50 millivolts prior to modification with the metal ion.

20. The substrate of claim 17, wherein the zeta potential of the modified nanoparticles is greater than the zeta potential of the first nanoparticles prior to modification.

21. The substrate of claim 20, wherein the zeta potential of the modified particles is from about −5 millivolts to about −15 millivolts.

22. The substrate of claim 17, wherein the metal ion is adsorbed onto a surface of the first nanoparticles.

23. The substrate of claim 17, wherein the metal ion forms a coordinate or covalent bond with the first nanoparticles.

24. The substrate of claim 17, wherein the first nanoparticles have a surface area of at least about 100 square meters per gram.

25. The substrate of claim 17, wherein the first and second nanoparticles have a size of less than about 500 nanometers.

26. The substrate of claim 17, wherein the first nanoparticles comprise silica.

27. The substrate of claim 17, wherein the second nanoparticles comprise alumina.

28. The substrate of claim 27, wherein the alumina is coated onto silica.

29. The substrate of claim 17, wherein the metal ion includes copper, silver, gold, iron, manganese, or combinations thereof.

30. The substrate of claim 17, wherein the substrate contains polyolefin fibers.

31. The substrate of claim 17, wherein the substrate is a spunbond web, meltblown web, or combination thereof.

32. The substrate of claim 17, wherein the substrate contains cellulosic fibers.

33. The substrate of claim 17, wherein the modified nanoparticles constitute from about 0.1 to about 10 wt.% of the substrate.

34. A personal care product comprising the substrate of claim 17.

35. Protective barrier clothing comprising the substrate of claim 17.

* * * * *